(12) United States Patent
Hanssen

(10) Patent No.: US 6,709,462 B2
(45) Date of Patent: Mar. 23, 2004

(54) ACETABULAR SHELL WITH SCREW ACCESS CHANNELS

(75) Inventor: Arlen D. Hanssen, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 3 days.

(21) Appl. No.: 10/044,044

(22) Filed: Jan. 11, 2002

(65) Prior Publication Data

US 2003/0135281 A1 Jul. 17, 2003

(51) Int. Cl.[7] .................................................. A61F 2/32
(52) U.S. Cl. .................................. 623/22.35; 623/22.34
(58) Field of Search ........................... 623/22.21, 22.32, 623/22.33, 22.34, 22.35, 22.36, 22.37, 20.34, 23.5

(56) References Cited

U.S. PATENT DOCUMENTS

| | | |
|---|---|---|
| 3,855,638 A | 12/1974 | Pilliar |
| 4,206,516 A | 6/1980 | Pilliar |
| 4,955,325 A | 9/1990 | Zarnowski et al. |
| 5,370,702 A | 12/1994 | Jones |
| 5,507,833 A | 4/1996 | Bohn |
| 5,571,198 A | 11/1996 | Drucker et al. |
| 5,609,648 A | 3/1997 | Oehy et al. |
| 5,645,606 A | 7/1997 | Oehy et al. |
| 5,734,959 A | 3/1998 | Krebs et al. |
| 5,782,929 A | 7/1998 | Sederholm |
| 5,876,456 A | 3/1999 | Sederholm et al. |
| 5,888,205 A * | 3/1999 | Pratt et al. ............... 623/23 |
| 5,925,077 A | 7/1999 | Williamson et al. |
| 5,935,174 A | 8/1999 | Dye |
| 6,013,104 A | 1/2000 | Kampner |
| 6,120,546 A | 9/2000 | Dye et al. |
| 6,152,962 A | 11/2000 | DeCarlo et al. |
| 6,207,218 B1 | 3/2001 | Layrolle et al. |
| 6,231,612 B1 | 5/2001 | Balay et al. |

* cited by examiner

*Primary Examiner*—Bruce E Snow
(74) *Attorney, Agent, or Firm*—Quarles & Brady LLP

(57) ABSTRACT

An outer shell for a socket of a joint prosthesis is disclosed. The outer shell includes an outer wall defining an outer surface of the shell and an inner wall defining an inner surface of the shell. The outer wall has pores to permit bone tissue to grow into the outer wall, and the inner surface of the shell engages the socket. The inner wall has access channels suitable for seating a bone screw. The access channels are closed off by an associated integral section of the shell. Preferably, each access channel is closed off by a section of the outer wall so that the shell retains maximal outer surface area for bone tissue ingrowth. When a number of bone screws are needed for affixation of the shell to bone, a number of locations for bone screws can be created in the shell by opening the closed access channels.

20 Claims, 3 Drawing Sheets

ACETABULAR SHELL WITH SCREW ACCESS CHANNELS

BACKGROUND OF THE INVENTION

1. Field of the Invention

This invention relates to an outer shell for a socket of a joint prosthesis, and in particular relates to an acetabular shell having closed off access channels within the inner aspect of the shell wherein the closed off section of each access channel can be removed for receipt of a bone screw or penetrated by a bone screw for screw fixation of the acetabular shell to bone.

2. Description of the Related Art

For many years now, prostheses have been implanted in the human body to repair or reconstruct all or part of an articulating skeletal joint, such as the hip joint. The hip joint includes the femur and the pelvis, each of which has a surface for articulation against an adjacent articulation surface of the other bone. The femur has a head having a convex, generally spherically contoured articulation surface. The pelvis includes an acetabulum having a concave, generally spherically contoured articulation surface. The articulation surfaces of the femur and the pelvis form a ball-and-socket type joint.

One or both of the articulation surfaces of the hip joint may fail to perform properly, requiring the defective natural articulation surface to be replaced with a prosthetic articulation surface. In an artificial hip joint, a femoral head and a femoral stem can be used to replace the natural head, stem, and articulating surface of the femur, and an acetabular cup can be used to replace the natural socket and articulating surface of the acetabulum of the pelvis. The artificial femoral stem and head may be an integral unitary component or separate modular components designed to be assembled together. The femoral head articulates directly against the natural acetabulum or the artificial acetabular cup. The acetabular cup component is received and fixed within the acetabulum of a pelvis. The pelvis is prepared to receive the acetabular cup by reaming a concavity in the acetabular bone. The acetabular cup component typically has an outer surface conforming to the concavity reamed in the acetabular bone of the pelvis, and an inner bearing cavity for receiving the head of the femoral component or a healthy femur. The head articulates in the bearing cavity of the acetabular cup.

One known type of acetabular cup includes an acetabular shell made of a bio-compatible metal, such as titanium or a titanium or cobalt alloy, and a bearing insert made of a material which allows the natural or artificial femur head to move about, such as a bio-compatible polymer (e.g. ultra-high molecular weight polyethylene). Some acetabular shells are attached to the acetabular bone using polymerizable synthetic cement, and others are attached to the bone using mechanical anchoring means such as screws. The shell also can be affixed by a combination of bone screws and bone cement. Still other acetabular shells can be attached to the acetabular bone using a "press-fit" shell in which the shell is inserted forcibly into the acetabular cavity. After the acetabular shell is implanted, the bearing insert is secured within the acetabular shell and the head of the femoral component or a healthy femur is positioned in the bearing insert.

If bone screw affixation is selected for the acetabular shell, the bone screws are driven into the acetabular bone through screw holes in the acetabular shell. Often, the acetabular shell is provided with more screw holes than typically would be used by the implanting physician. This provides a selection of sites for placement of the bone screws, as may be dictated by the condition of the patient's pelvic bone. Some of the provided screw holes may receive a screw while others do not. When the assembled hip prosthesis is loaded, unintended micromotion may occur between the acetabular shell and the bearing insert. This micromotion may form wear debris (e.g., fine polyethylene or metal particles) from the rubbing of the acetabular shell and the bearing insert. It has been reported that this wear debris may blend with synovial fluid and thereby migrate out of the screw holes of the acetabular shell and into the acetabular bone region. The wear debris may cause osteolysis, which can lead to bone resorption and loosening of the bone screws over time.

In order to limit the migration of wear debris into the acetabular bone region, it has been proposed to seal or cover the unused screw holes of an acetabular shell. For example, U.S. Pat. No. 5,925,077 shows an acetabular shell component having preinstalled plugs which plug screw holes in the acetabular shell. The plugs may be a plug that is press fit into a screw hole, or a disk shaped plug that is bonded over a screw hole, or a plug that is snap fit into a screw hole. If it is determined that fixation screws are needed for implantation of the acetabular shell, selected plugs may be removed using a removal instrument. U.S. Pat. No. 5,782,929 shows an acetabular shell having plugs which plug screw holes in the acetabular shell. The screw hole plugs are press fit and then sintered into the screw hole. The screw hole plugs can be removed by the surgeon to create an unplugged hole for receiving screws. U.S. Pat. No. 5,571,198 shows an acetabular shell having screw holes which are plugged with threaded screw hole plugs. The screw hole plugs can be removed by the surgeon to create an unplugged screw hole that can receive a screw. U.S. Pat. No. 5,370,702 shows an acetabular shell having removable portions that a surgeon may grasp by a post and pull out of the shell thereby creating a screw hole in the shell. U.S. Pat. Nos. 6,152,962, 6,120, 546, 5,935,174, 5,876,456, 5,645,606, 5,609,648 and 4,955, 325 all show other examples of the use of plugs to fill the screw holes in a acetabular shell. Thus, depending on the construction of the acetabular shell, the surgeon may either plug unused open screw holes or open plugged screw holes at the time of implantation of the acetabular shell.

The prosthetic systems of the above patents all provide various solutions to the problems associated with the migration of wear debris through screw holes of an acetabular shell and into the acetabular bone region. However, these prosthetic systems do have disadvantages. For instance, each of these acetabular shell implants requires the use of multiple plugs that must secured (at the manufacturing site or in the operating room) into holes in the acetabular shell by threading, sintering, press-fitting, or other similar technique. Acetabular shells that are supplied from the manufacturer with plugged screw holes can be quite expensive given the large number of manufacturing operations required to assemble the plugs into the screw holes of the acetabular shell and the costs associated with the manufacture of a large number of plugs. Acetabular shells that are supplied with plugged screw holes may also necessitate the use of special surgical instruments to unplug the screw holes in the operating room. Acetabular shells that are supplied from the manufacturer with unplugged screw holes require the hospital to purchase and store a large number of plugs (which typically will vary among manufacturer). Then, the surgeon must assemble the plugs into the screw holes during the implantation procedure. This usually requires the use of special instruments to insert the plugs into the screw holes.

Also, these known acetabular shells may not provide for maximum surface area for potential tissue ingrowth on the outer surface of the acetabular shell as the screw hole plugs may be positioned below the outer surface of the acetabular shell. When screw hole plugs are positioned below the outer surface of the acetabular shell, tissue ingrowth is limited to the outer surface of acetabular shell surrounding the screw hole plugs. Furthermore, these known acetabular shells may only include a limited number of screw holes, given the increased manufacturing costs associated with manufacturing additional plugs and inserting the plugs into a large number of screw holes. This limits the surgeon's choices for bone screw location such that the quality and number of screws with excellent bone purchase may be less than is deemed desirable by the surgeon. Furthermore, the location of the few screw holes in these known acetabular shells may be incongruous with the location of available bone stock.

Therefore, there is a continuing need for an improved acetabular shell that allows for screw fixation of the acetabular shell to bone at multiple locations and that limits migration of wear debris out of the screw holes of the acetabular shell and into the acetabular bone region. In particular, there is a need for an acetabular shell that provides a large selection of available locations for screw fixation, that retains maximum outer surface area for bone tissue ingrowth, and that can also limit migration of wear debris out of the screw holes of the acetabular shell and into the acetabular bone region.

SUMMARY OF THE INVENTION

The foregoing needs are met by an outer shell for a socket of a joint prosthesis in accordance with the invention. The outer shell includes an outer wall defining an outer surface of the outer shell and an inner wall defining an inner surface of the outer shell. The outer wall has pores of a size sufficient to permit bone tissue to grow into the outer wall and the inner surface of the outer shell is suitable for engaging an outer surface of the socket. Optionally, the inner wall is joined to the outer wall thereby forming an interfacial boundary between the inner wall and the outer wall. The inner wall has a plurality of access channels suitable for seating a bone screw. There is no limit on the number of access channels and therefore, the shell provides a large selection of available locations for screw fixation to available bone. In one embodiment, the outer shell is an acetabular shell for the socket of a hip joint prosthesis.

At least a portion of the access channels of the outer shell are closed off by an associated integral section of the outer shell such that the portion of access channels do not extend through the outer surface of the outer shell. Each associated integral section includes at least a section of the outer wall. At least one of the associated integral sections may also include a section of the inner wall. At least one of the associated integral sections may also consist of the entire cross-sectional width of the outer wall. In other words, the particular section of the outer shell that closes off each access channel may comprise: (i) a section of the outer wall having less than the full cross-sectional width of the outer wall; (ii) a section of the outer wall having the full cross-sectional width of the outer wall; or (iii) a section of the outer wall having the full cross-sectional width of the outer wall and at least a cross-section of the inner wall. Each associated integral section is suitable for penetration with a self tapping bone screw or with a drill bit (or similar puncturing instrument) such that a surgeon may insert and seat bone screws in the opened access channel.

The outer wall comprises an integral unitary structure such that each closed off access channel is closed off by at least a section of the outer wall as described above. Therefore, there is no need for plugs or inserts to close off any access channels in the shell. The pores of the outer wall may be formed by interconnected metallic particles, such as particles formed from titanium, titanium alloys, cobalt alloys, stainless steel alloys, or tantalum alloys. Optionally, the outer surface of the outer shell has a plurality of depressions for mechanical interlocking with bone tissue, and the outer surface of the outer shell may also have a coating of a bone ingrowth promoting material such as hydroxyapatite. Because each closed off access channel is closed off by at least a section of the outer wall, the shell retains maximal surface area for bone tissue ingrowth on the outer surface of the shell. In other words, there are no plugs or inserts that hinder bone tissue ingrowth.

It is therefore an advantage of the present invention to provide an acetabular shell that limits migration of wear debris out of screw holes of the acetabular shell and into the acetabular bone region and that allows for screw fixation of the acetabular shell to bone at multiple locations.

It is another advantage of the present invention to provide an acetabular shell that limits migration of wear debris out of screw holes of the acetabular shell and that retains maximum outer surface area for bone tissue ingrowth.

It is a further advantage of the present invention to provide an acetabular shell that limits migration of wear debris out of screw holes of the acetabular shell and that does not require the use of multiple screw hole plugs or specialized plug removal equipment.

It is a yet another advantage of the present invention to provide an acetabular shell that allows for both screw fixation and press-fit implantation and that retains maximum outer surface area for bone tissue ingrowth.

BRIEF DESCRIPTION OF THE DRAWINGS

These and other features, aspects, and advantages of the present invention will become better understood upon consideration of the following detailed description, appended claims and drawings where:

Figure 1:
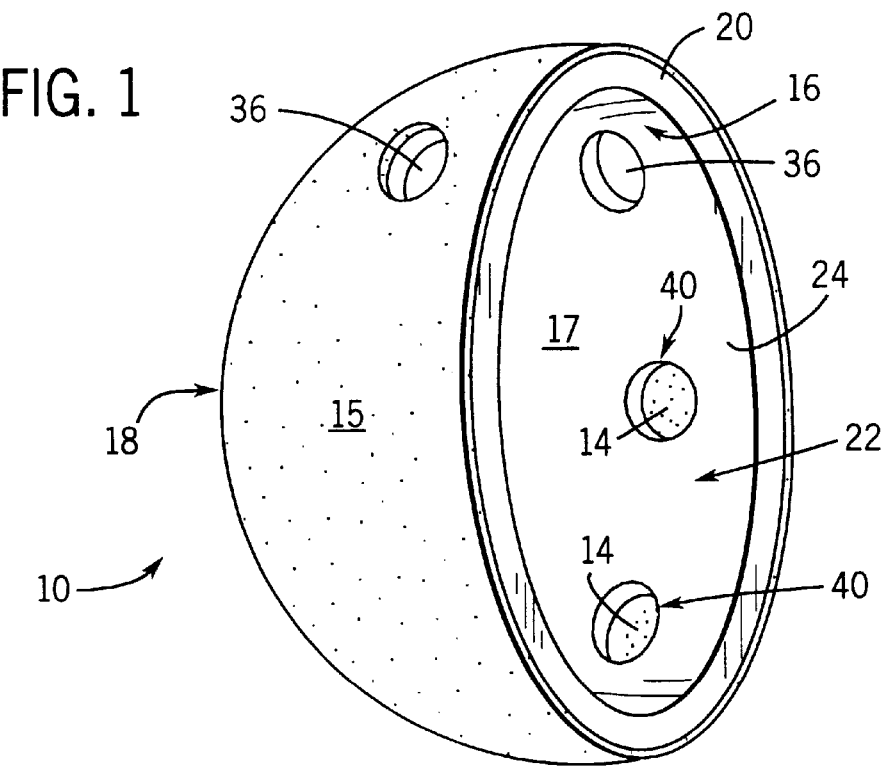
FIG. 1 is a perspective view of an acetabular shell according to the invention.

It should be understood that the drawings are not necessarily to scale, and details which are not necessary for an understanding of the present invention or which render other details difficult to perceive may have been omitted. Like reference numerals will be used to refer to like or similar parts from Figure to Figure in the following description of the invention.

DETAILED DESCRIPTION OF THE INVENTION

Referring to FIGS. 1–5, an example embodiment of the present invention is illustrated as an implantable acetabular shell component of a hip joint prosthesis. The illustrated acetabular shell is useful as one component of a well-known hip joint prosthesis that includes an acetabular shell and an associated insert bearing liner, and a femoral stem and an associated spherical head. The spherical head, fixed to the femoral stem, articulates in a ball-and-socket arrangement within the insert bearing liner, with the insert bearing liner being essentially fixed within the acetabular shell. The femoral stem and acetabular shell are fixed to bone of the proximal femur and pelvic acetabulum, respectively. Only the acetabular shell is described in detail herein, as the various types and forms of insert bearing liners and the means for affixing such insert bearing liners within an acetabular shell are well understood in the art.

The illustrated acetabular shell is particularly advantageous for preventing potentially osteolytic wear debris particles from migrating out of the acetabular shell, when used with an insert bearing liner made of material subject to wear, such as ultra-high molecular weight polyethylene. It should be understood that the present invention is not limited to the acetabular shell illustrated and can be used as the outer shell for a socket of a joint prosthesis used in the repair of any joint that requires articulating movement. Further, the present invention can be used in primary surgery, in which a prosthesis is being used to reconstruct a joint for the first time, as well as in revision surgery, in which a previously-implanted prosthesis is being replaced with another prosthesis.

The acetabular shell 10 is shaped generally as a hemispherical cup having a shell wall 12 comprising an outer wall 14 and a inner wall 16. The acetabular shell 10 has a dome region 18 at the apex of shell wall 12 and an annular rim 20 at the distal end of shell wall 12. The outer wall 14 of shell wall 12 defines an outer surface 15 of the acetabular shell 10. The inner wall 16 of shell wall 12 defines an inner surface 17 which defines a shell cavity 22 having an opening 24 into and through which a bearing insert (not shown) can be received. The preferred bearing insert is made of ultra high molecular weight polyethylene and has a partially spherical bearing cavity that opens distally for receiving a spherical head of a femoral component (not shown) in a ball-and-socket articulating relationship.

The inner wall 16 may be formed from a metal alloy such as a titanium alloy (e.g., titanium-6-aluminum-4-vanadium), a cobalt alloy, a stainless steel alloy or a tantalum alloy; a nonresorbable ceramic such as aluminum oxide or zirconia; a nonresorbable polymeric material such as polyethylene; or a nonresorbable composite material such as a carbon fiber-reinforced polymers (e.g., polysulfone). Preferably, the inner wall 16 of the acetabular cup implant is formed from a metal alloy, and most preferably, is formed from a titanium or cobalt alloy.

The outer wall 14 comprises a porous material, and preferably comprises a porous metallic material having a network of interconnected pores distributed throughout particles of the metallic material. The particle size of the metallic particles is chosen to ensure that the resulting interstitial pore size is at least sufficient to permit bone tissue to grow into the porous material for incorporation of the acetabular shell 10 into the acetabular bone. Preferably, the metallic particles are formed from titanium, titanium alloys, cobalt alloys, stainless steel alloys, tantalum alloys, and mixtures thereof. Various methods are known for forming the outer wall 14 of porous material on the inner wall 16, such as the methods described in U.S. Pat. Nos. 5,734,959, 4,206,516 and 3,855,638. The outer surface 15 of the outer wall 14 may also include a textured surface comprising a plurality depressions such as grooves, dimples, or the like. Further, the outer surface 15 of the outer wall 14 may also have a coating of a bone ingrowth promoting material such as hydroxyapatite ($Ca_{10}(PO_4)_6OH_2$), a calcium phosphate (e.g., tricalcium phosphate ($Ca_3(PO_4)_2$)), growth factors, bone morphogenic proteins, and mixtures thereof.

Figure 2:
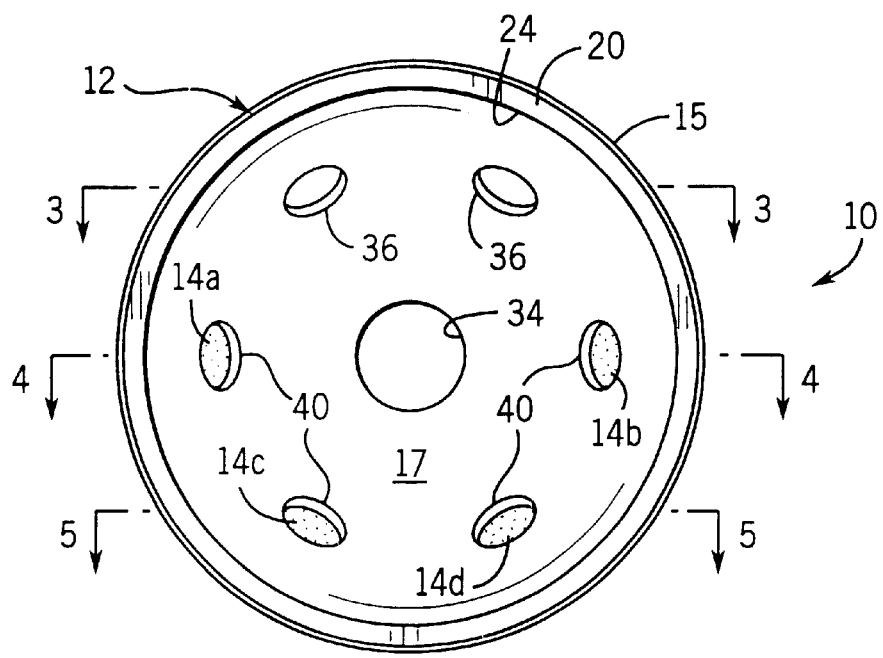
FIG. 2 is a front view of the acetabular shell of FIG. 1.
Figure 3:
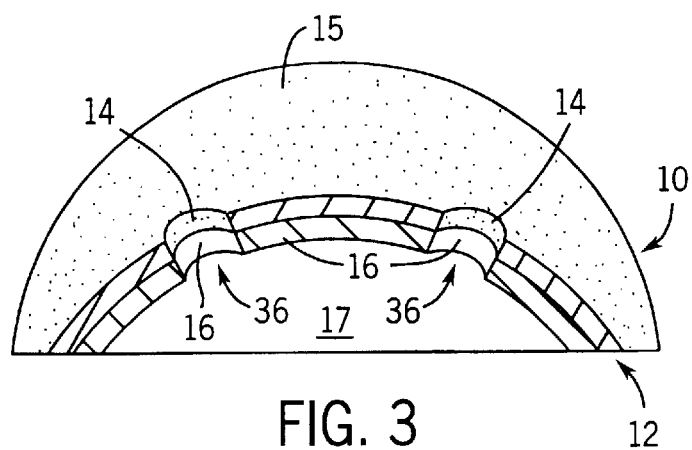
FIG. 3 is a cross-sectional view of the acetabular shell of FIG. 2 taken along line 3—3 in FIG. 2.

Referring to FIGS. 2 and 3, the acetabular shell 10 may be provided with a plurality of screw holes 36 which extend through the inner wall 16 and the outer wall 14 of the shell wall 12 in various locations. The inner surface of each screw hole 36 may be configured to receive and seat a bone screw (not shown) of a predetermined shape. For instance, the bone screw may include a head and a threaded shank wherein the undersurface of the head of the bone screw (i.e., that portion of the head adjacent the shank) has a truncated cone shape. In this example, the inner surface of the screw holes 36 would be shaped with a countersink to allow the undersurface of the bone screw to seat on the inner surface of the upper portion of the screw hole 36. Looking at FIG. 3, it can be seen that the screw hole 36 extends completely through the acetabular shell 10, that is, from the inner surface 17 of the acetabular shell 10 to the outer surface 15 of the acetabular shell 10. The screw holes 36 are optional features of the acetabular shell 10 and are not required for use of the acetabular shell 10.

Figure 4:
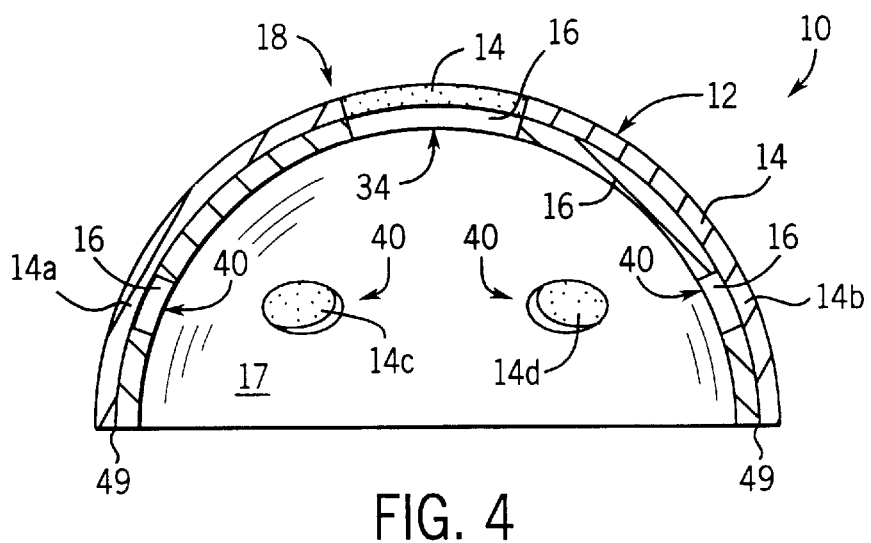
FIG. 4 is a cross-sectional view of the acetabular shell of FIG. 2 taken along line 4—4 in FIG. 2.

Referring to FIGS. 2 and 4, the acetabular shell 10 may also include a dome hole 34 centered at the apex of dome region 18. The dome hole 34 is configured to serve as an engagement interface for an instrument (not shown) for holding and positioning acetabular shell 10. Typically, such an instrument is used by the implanting physician to securely grasp the acetabular shell and place it in the reamed acetabulum. Looking at FIG. 4, it can be seen that the dome hole 34 extends completely through the acetabular shell 10, that is, from the inner surface 17 of the acetabular shell 10 to the outer surface 15 of the acetabular shell 10. The dome hole 34 is optional feature of the acetabular shell 10 is not required for use of the acetabular shell 10.

Figure 5:
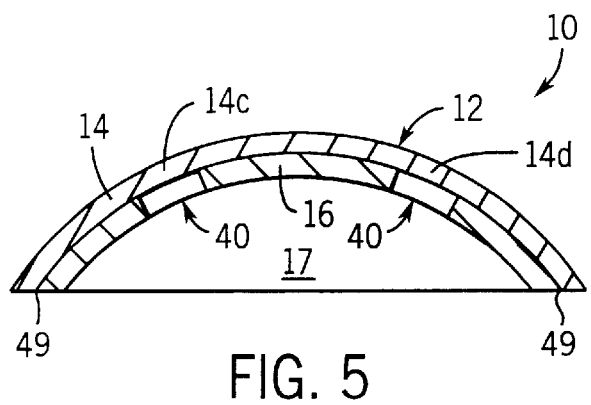
FIG. 5 is a cross-sectional view of the acetabular shell of FIG. 2 taken along line 5—5 in FIG. 2.

Referring to FIGS. 2, 4 and 5, the acetabular shell 10 is provided with a plurality of access channels 40 which extend through the inner wall 16 but not the outer wall 14 of the shell wall 12 at various locations. The acetabular shell 10 shown in FIGS. 2, 4 and 5 has four access channels 40 at specific locations. However, it should be understood that the acetabular shell 10 can have any number of access channels 40 at any location in the acetabular shell 10 (i.e., four access channels 40 have been shown for illustrative purposes only). Like the optional screw holes 36, the inner surface of each access channel 40 may be shaped (such as in a truncated cone or a generally spherical shape) to provide a seat for the undersurface of the head of a bone screw.

Looking now at FIGS. 4 and 5, it can be seen that each access channel 40 shown extends from the inner surface 17 of the acetabular shell 10 to a boundary 49 formed at the junction of the inner wall 16 and the outer wall 14. The access channels 40 shown are closed off by sections 14a, 14b, 14c, and 14d of the outer wall 14 such that the access channels 40 do not extend through the outer wall 14 to the outer surface 15 of the acetabular shell 10. The sections 14a, 14b, 14c, and 14d of the outer wall 14 consist of cylindrical regions bounded by the outer surface 15 of the acetabular shell 10, the boundary 49 at the junction of the inner wall 16 and the outer wall 14, and an imaginary surface extending from the inner surface of the access channel 40 to the outer surface 15 of the acetabular shell 10. The sections 14a, 14b, 14c, and 14d of the outer wall 14 are completely integral with the outer wall 14 as the outer wall 14 is an integral unitary structure, and each section 14a, 14b, 14c, and 14d of the outer wall 14 is associated with an access channel 40.

Figure 5A:
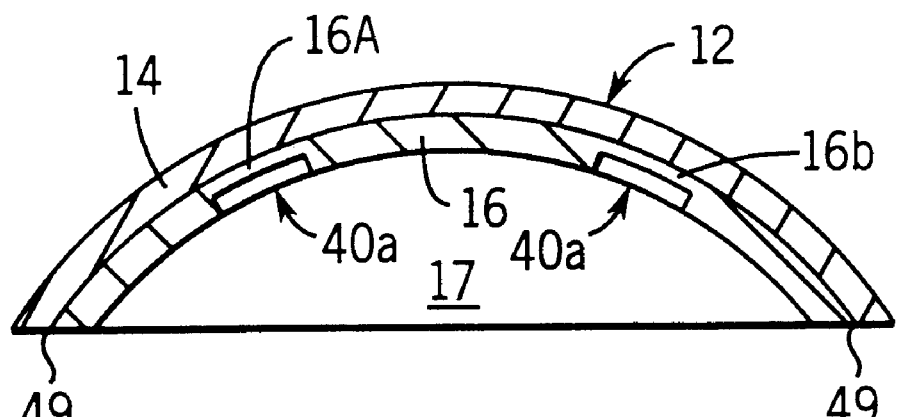
FIG. 5A is a cross-sectional view similar to that of FIG. 5 of another acetabular shell according to the invention.
Figure 5B:
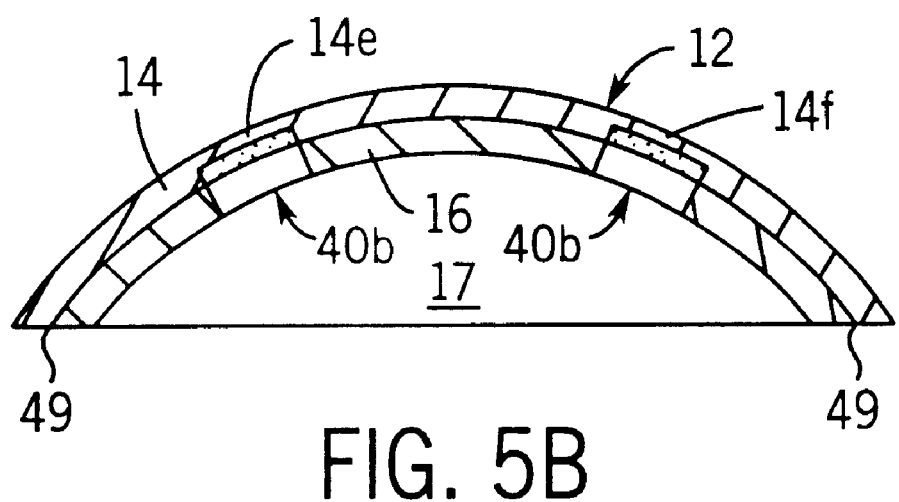
FIG. 5B is a cross-sectional view similar to that of FIG. 5 of yet another acetabular shell according to the invention.

In FIG. 5A, alternative access channels 40a are shown wherein the access channels 40a are closed off by sections which comprise sections 14c and 14d of the outer wall 14 (shown in FIG. 5) and sections 16a and 16b of the inner wall 16 (shown in FIG. 5b). In FIG. 5B, alternative access channels 40b are shown wherein the access channels 40b are closed off by sections 14e and 14f of the outer wall 14. The sections 14e and 14f of the outer wall 14 have a reduced cross-sectional width compared to the sections 14a, 14b, 14c, and 14d of the outer wall 14 shown in FIG. 5. In other words, the sections 14e and 14f of the outer wall 14 do not extend inward to the boundary 49 at the junction of the inner wall 16 and the outer wall 14. It can be appreciated that any number and combination of access channels 40, 40a and 40b can be used in the acetabular shell 10. Also, some of the access channels 40, 40a and 40b may not be closed off (i.e., the access channels extend from the inner surface 17 of the outer shell 10 through the outer surface 15 of the outer shell 10).

Comparing the access channels 40 of FIG. 5, the access channels 40a of FIG. 5A and the access channels 40b of FIG. 5B, it can be seen that the access channels 40, 40a and 40b can be closed off by various combinations of sections of the outer wall 14 and the inner wall 16. However, in each example, at least a section of the outer wall 16 comprises a portion of the section that is used to close off the access channels 40, 40a and 40b. Therefore, every access channel 40, 40a and 40b will be closed off by a section of the outer wall 16 that is available for bone tissue ingrowth after implantation of the acetabular shell 10. If the acetabular shell 10 were to only include access channels 40, 40a and 40b (i.e., not a dome hole 34 or any screw holes 36), the entire unitary outer surface 15 of the acetabular shell 10 would be available for bone tissue ingrowth after implantation of the acetabular shell 10.

The acetabular shell 10 may be implanted in a hip bone as follows. First, the acetabular cavity of the hip bone is inspected and tools (such as a reamer) may be used to clean material out of the acetabular cavity. Once the acetabular cavity has been prepared, the surgeon can then analyze the remaining bone stock to assess possible points of screw fixation of the acetabular shell 10. The surgeon then has a number of options. The surgeon may decide to rely on a "press-fit" for implantation of the acetabular shell 10 into the end portion of the acetabular cavity of the hip bone. In this case, the acetabular shell 10 is implanted without modification and the entire outer surface 15 of the acetabular shell 10 (with the exception of the areas bounded by any dome hole 34 or any screw holes 36) is available for bone tissue ingrowth.

If the surgeon decides to rely screw fixation, the surgeon has a number of options. If screw holes 36 are present in the acetabular shell 10, the surgeon can use these screw holes 36 as locations for a bone screw. If no screw holes 36 or not enough screw holes 36 are present in the acetabular shell 10, the surgeon can use a drill or similar puncturing instrument to open the closed off section of any number of access channels 40, 40a and 40b present in the acetabular shell 10. The opened access channels 40, 40a and 40b then can be used as locations for a bone screw. If no screw holes 36 or not enough screw holes 36 are present in the acetabular shell 10, the surgeon also has the option to impact the acetabular shell 10 into the bone and then use self-tapping screws to penetrate through the closed off section of any number of access channels 40, 40a and 40b and into the bone.

An acetabular shell 10 according to the invention having a number of closed off access channels 40, 40a and 40b has several advantages. First, in instances where no or few bone screws are needed for affixation of the acetabular shell 10 to bone, maximum outer surface area of the acetabular shell 10 is available for bone tissue ingrowth as the access channels 40, 40a and 40b are closed off by at least a section of the outer wall 14. In prior known acetabular shells, the lack of closed off holes or the use of hole plugs has hindered bone tissue ingrowth onto the acetabular shell. Second, where a number of bone screws are needed for affixation of the acetabular shell 10 to bone, the access channels 40, 40a, 40b can be opened without specialized plug removal instruments to create a large number of locations for bone screws. However, even after creation of a large number of locations for bone screws, the remaining outer surface area of the acetabular shell 10 (including the opened areas overlying the access channels 40, 40a and 40b) is still available for bone tissue ingrowth and the unused access channels effectively block egress of wear debris into the retroacetabular region.

While the implantation of an acetabular shell has been illustrated and described herein, one skilled in the art will appreciate that the present invention can be practiced by other than the described embodiments, which have been presented for purposes of illustration and not of limitation. For instance, the methods and prostheses according to the invention can be used as part of the repair of other articulating joints such as the shoulder. Accordingly, the scope of the appended claims should not be limited to the description of the embodiments contained herein.

What is claimed is:

1. An outer shell for a socket of a joint prosthesis, the outer shell comprising:

an outer wall having pores of a size sufficient to permit bone tissue to grow into the outer wall, the outer wall defining an outer surface of the outer shell; and an inner wall defining an inner surface of the outer shell, the inner surface of the outer shell suitable for engaging an outer surface of the socket, the inner wall having at least one access channel extending through the inner wall, each access channel being suitable for seating a bone screw, wherein at least one access channel that extends through the inner wall is closed off by an associated integral section of the outer wall so as to not extend through the outer surface of the outer shell.

2. The outer shell of claim 1 wherein:

the inner wall is joined to the outer wall such that a boundary is formed between the inner wall and the outer wall, and at least one associated integral section of the outer wall consists of a section of the outer wall extending from the boundary to the outer surface of the outer shell.

3. The outer shell of claim 1 wherein:

the inner wall is joined to the outer wall such that a boundary is formed between the inner wall and the outer wall, and at least one associated integral section of the outer wall consists of a section of the outer wall extending from the outer surface of the outer shell to a position between the outer surface and the boundary.

4. The outer shell of claim 1 wherein:

at least one of the access channels extends from the inner surface of the outer shell to the outer surface of the outer shell.

5. The outer shell of claim 1 wherein:

the inner wall has a plurality of access channels extending through the inner wall, and a plurality of access channels that extend through the inner wall are closed off by an associated integral section of the outer wall so as to not extend through the outer surface of the outer shell.

6. The outer shell of claim 1 wherein:

each associated integral section is suitable for penetration with a self tapping bone screw or a drill bit.

7. The outer shell of claim 1 wherein:

the outer wall comprises interconnected metallic particles that define the pores, the metallic particles comprising titanium, titanium alloys, cobalt alloys, stainless steel alloys, tantalum alloys, or mixtures thereof.

8. The outer shell of claim 1 wherein:

the inner wall comprises titanium, titanium alloys, cobalt alloys, stainless steel alloys, tantalum alloys, or mixtures thereof.

9. The outer shell of claim 1 wherein:

the outer wall consists of an integral unitary structure.

10. The outer shell of claim 1 wherein:

the outer surface of the outer shell has a plurality of depressions.

11. The outer shell of claim 1 wherein:

the outer surface of the outer shell has a coating of a bone ingrowth promoting material.

12. The outer shell of claim 11 wherein:

the bone ingrowth promoting material is selected from hydroxyapatite, calcium phosphates, growth factors, bone morphogenic proteins, and mixtures thereof.

13. An outer shell for a socket of a joint prosthesis, the outer shell comprising:

an outer wall having pores of a size sufficient to permit bone tissue to grow into the outer wall, the outer wall defining an outer surface of the outer shell; and an inner wall defining an inner surface of the outer shell, the inner surface of the outer shell suitable for engaging an outer surface of the socket, the inner wall having a plurality of access channels suitable for seating a bone screw, wherein at least one access channel is closed off by an associated integral section of the outer shell so as to not extend through the outer surface of the outer shell, wherein the associated integral section includes a section of the inner wall and a section of the outer wall, and wherein at least one of the access channels extends completely through the inner wall and the outer wall.

14. The outer shell of claim 13 wherein:

each associated integral section is suitable for penetration with a self tapping bone screw or a drill bit.

15. The outer shell of claim 13 wherein:

the outer wall comprises interconnected metallic particles that define the pores, the metallic particles comprising titanium, titanium alloys, cobalt alloys, stainless steel alloys, tantalum alloys, or mixtures thereof.

16. The outer shell of claim 13 wherein:

the inner wall comprises titanium, titanium alloys, cobalt alloys, stainless steel alloys, tantalum alloys, or mixtures thereof.

17. The outer shell of claim 13 wherein:

the outer wall consists of an integral unitary structure.

18. The outer shell of claim 13 wherein:

the outer surface of the outer shell has a plurality of depressions.

19. The outer shell of claim 13 wherein:

the outer surface of the outer shell has a coating of a bone ingrowth promoting material.

20. The outer shell of claim 19 wherein:

the bone ingrowth promoting material is selected from hydroxyapatite, calcium phosphates, growth factors, bone morphogenic proteins, and mixtures thereof.

* * * * *